(12) United States Patent
Hwang et al.

(10) Patent No.: US 8,642,646 B2
(45) Date of Patent: Feb. 4, 2014

(54) METHOD AND COMPOSITION FOR TREATING ACNE USING LIGNAN COMPOUNDS

(75) Inventors: Jae-Kwan Hwang, Gyeonggi-do (KR);
Jae-Youn Chung, Seoul (KR);
Hee-Chul Chung, Gyeonggi-do (KR);
Kyung-Min Park, Gyeonggi-do (KR)

(73) Assignees: New Tree Industry Co., Ltd., Sungnam (KR); Jae-Kwan Hwang, Goyang (KR)

( * ) Notice: Subject to any disclaimer, the term of this patent is extended or adjusted under 35 U.S.C. 154(b) by 1873 days.

(21) Appl. No.: 10/585,553

(22) PCT Filed: Jan. 7, 2005

(86) PCT No.: PCT/KR2005/000045
§ 371 (c)(1),
(2), (4) Date: Jul. 6, 2006

(87) PCT Pub. No.: WO2005/070402
PCT Pub. Date: Aug. 4, 2005

(65) Prior Publication Data
US 2009/0192217 A1    Jul. 30, 2009

(30) Foreign Application Priority Data
Jan. 8, 2004    (KR) .................. 10-2004-0001207

(51) Int. Cl.
*A61K 8/97*    (2006.01)
*A61K 31/36*   (2006.01)
*A61Q 19/00*   (2006.01)

(52) U.S. Cl.
USPC ........... 514/464; 514/859; 514/731; 514/886; 514/18.6; 424/776; 424/725; 549/445

(58) Field of Classification Search
None
See application file for complete search history.

(56) References Cited

FOREIGN PATENT DOCUMENTS

| EP | 297733 A2 | 1/1989 |
|---|---|---|
| WO | WO 88/01509 A1 | 3/1988 |
| WO | WO 88/03806 A1 | 6/1998 |
| WO | WO 03/028692 A2 | 4/2003 |

OTHER PUBLICATIONS

Sadhu et al, Chem Pharm Bull. 51 (5) 595-598, 2003.*
Akamatsu et al., Dermatology, 1998; 196: pp. 82-85.*
Dorman et al, Journal of Applied Microbiology, 2000, 88, 308-316.*
Woo et al, Phytochemistry, vol. 26, issue 5, 1987 pp. 1542-1543, Abstract only.*
Deac et al. abstract, Igiena (1970), vol. 19 (3), pp. 167-73.*
Gibson (Journal of Antimicrobial chemotherapy, 1980, pp. 538-570.*
Nakatani et al., "Diaryldimethylbutane Lignans From Myristica Argentea and Their Antimicrobial Action Against *Streptococcus mutans*'," Phytochemistry, 27(10): 3127-9 (1998).

* cited by examiner

*Primary Examiner* — Savitha Rao
(74) *Attorney, Agent, or Firm* — Joseph H. Kim; JHK Law (57) ABSTRACT

The present invention relates to a method and composition for treating acne using lignan compounds represented by Formula 1. More particularly, the invention relates to an antibacterial composition against acne-causing bacteria, containing lignan compounds represented by Formula 1, as well as a method for treating acne using the same. The lignan compounds represented by Formula 1 are excellent not only in the antibacterial activity of inhibiting the growth of acne-causing bacteria, but also in thermal stability. Accordingly, the lignan compounds may be useful as antibacterial agents against the acne-causing bacteria, and acne treatment agents.

2 Claims, 7 Drawing Sheets

METHOD AND COMPOSITION FOR TREATING ACNE USING LIGNAN COMPOUNDS

TECHNICAL FIELD

The present invention relates to a method and composition for treating acne using lignan compounds represented by Formula 1. More particularly, the present invention relates to an antibacterial composition against acne-causing bacteria, which contains lignan compounds represented by Formula 1, as well as a method for treating acne using the same.

BACKGROUND ART

Acne is a very common skin disorder caused by an inflammatory disease of the hair follicles and sebaceous glands. It causes inflammation in the hair follicles of the facial skin of teenagers and young adults. In these days, however, the age distribution of people affected by acne becomes wider and wider due to air pollution, sex hormone unbalance, drug abuse, stress, internal disease, etc. For adolescents, the secretion of male sex hormones (androgens) increases in both boys and girls. These hormones stimulate the sebaceous glands, located next to the hair follicles, and cause them to enlarge and to produce more sebum. At the same time, the surface layer of the skin around the pores becomes thick and sticky, resulting in narrowed or blocked pores. As a result, sebum accumulates within the hair follicles, and bacteria present in the hair follicles multiply, leading to inflammation.

Microorganisms that cause acne and inflammation include *Propionibacterium acnes, Staphylococcus aureus, Staphylococcus epidermis*, and the like. (Raman A. et al., *Lett. Appl. Microbiol.*, 21: 242-245, 1995). They are also found in the normal skin, and particularly, *Propionibacterium acnes* is the main bacterium causing acne. These microorganisms enter into the hair follicles through the follicular ducts, and inhabit the hair follicles deep while decomposing sebum to produce free fatty acids. Secondary infection of the infected sites with *Staphylococcus* strains results in red swelling and pus production.

The antibacterial agents, such as benzoyl peroxide, salicylic acid, benzalkonium chloride, phenol, tetracycline or erythromycin have been used to inhibit bacteria which cause acne and inflammatory skin disease of the hair follicles and sebaceous glands. Although using antibacterial agents such as tetracycline are effective for skin treatment, it has been known to have a high possibility of causing side effects, such as the appearance of strains resistant to *Propionibacterium*, and photosensitive disorders (Gollnick, H. et al., *Dermatology*, 196: 119-125, 1998). Furthermore, the salicylic acid preparations mainly effective for the removal of keratin cannot be used for purulent dermatitis and can cause skin flare and erythema. In addition, the benzoyl peroxide preparations for inhibiting pyogenic bacteria are frequently reported to cause side effects, such as allergic dermatitis and erythema, and are known to be unsuccessful in curing acne completely.

Recently, natural substances, such as tea tree oil, royal jelly extract, and ginseng extract, are used to treat acne. However, these natural substances do not comprise a single compound. Thus, other substances added during processes of formulating them into skin external preparations or cosmetics can result in a rapid reduction in the antibacterial activity of the natural substances. Furthermore, the antibacterial spectrum of the natural substances is not so broad that they cannot effectively show antibacterial activity against *Staphylococcus* strains causing acne. Particularly, the naturally occurring antibacterial substances have a problem in that it is difficult to formulate them, since, upon heating, they lose a large part of their active ingredients by evaporation or have insufficient thermal stability, leading to a rapid reduction in their antibacterial activity (Higaki, S. et al., *J. Dermatology*, 23: 310-314, 1996).

Lignans are the group of natural substances where n-phenylpropanes are linked by the β-site of n-propyl side chains. Their pharmaceutical effects are known with respect to blood glucose lowering effects (Korean Patent Laid-Open Publication No. 2003-0064919), anti-inflammatory effects (Korean Patent Laid-Open Publication No. 2003-0035124), and the like. Macelignan, a typical lignan compound found in *Myristica fragrans* (Tuchinda P. et al., *Phytochemistry*, 59: 169-173, 2002), was reported to have the caspase-3-activating activity of inducing apoptosis (Park B. Y. et al., *Biol. Pharm. Bull.*, 27(8): 1305-1307, 2004), and antioxidative activity (Sadhu, S. K. et al., *Chem. Pharm. Bull.*, 51(9): 595-598, 2003). However, there is still no report on the antibacterial activity of lignan compounds represented by Formula 1, including macelignan, against acne-causing bacteria.

DISCLOSURE OF THE INVENTION

Therefore, the present inventors have performed long-term investigations in an attempt to discover natural product-derived compounds having powerful antibacterial activity against the acne-causing bacteria, and consequently, found that lignan compounds isolated from *Myristica fragrance* show not only excellent antibacterial activity against the acne-causing bacteria but also excellent thermal stability. Based upon this finding, the present invention has been completed.

It is an object of the present invention to provide lignan compounds represented by Formula 1, which show antibacterial activity against acne-causing bacteria, as well as an antibacterial composition against acne-causing bacteria and a composition for treating acne.

Another object of the present invention is to provide methods for inhibiting the growth of acne-causing bacteria and for treating acne, which comprise administering lignan compounds represented by Formula 1 to a subject in need thereof.

Still another object of the present invention is to provide the uses of lignan compounds represented by Formula 1 for preparing antibacterial agents against acne-causing bacteria and for preparing acne treatment agent.

To achieve the above objects, in one aspect, the present invention provides an antibacterial composition and an acne treatment composition, which contain lignan (2,3-dibenzylbutane) compounds represented by Formula 1 or their pharmaceutically acceptable salts, which have antibacterial activity against acne-causing bacteria selected from the group consisting of *Propionibacterium acnes, Staphylococcus aureus*, and *Staphylococcus epidermis*.

[Formula 1]

wherein each of $R_1$ and $R_2$ independently represents a $C_{1-5}$ alkoxy group or a hydroxyl group, and $R_3$ represents or In another aspect, the present invention provides a method for inhibiting the growth of acne-causing bacteria selected from the group consisting of *Propionibacterium acnes, Staphylococcus aureus* and *Staphylococcus epidermis*, and a method for treating acne, in which each of the methods comprises administering an effective amount of lignan compounds represented by Formula 1 to a subject in need thereof.

In another aspect, the present invention provides the uses of lignan compounds represented by Formula 1 for preparing antibacterial agents against acne-causing bacteria selected from the group consisting of *Propionibacterium acnes, Staphylococcus aureus*, and *Staphylococcus epidermis*, and for preparing acne treatment agents.

As used herein, the term "effective amount" means the amount of the inventive lignan compounds, which is sufficient to show antibacterial activity against acne-causing bacteria in a subject so as to allow effective treatment of acne.

As used herein, the term "subject" means mammals, particularly animals including human beings. The subject may be patients requiring treatment.

Hereinafter, the present invention will be described in detail.

The present invention is characterized by providing the antibacterial use of lignan compounds represented by Formula 1, against acne-causing bacteria.

The lignan compounds according to the present invention are represented by Formula 1 below:

[Formula 1]

wherein each of $R_1$ and $R_2$ independently represents a $C_{1-5}$ alkoxy group or a hydroxyl group, and $R_3$ represents A preferred example of the lignan compounds according to the present invention may be macelignan [(8R,8'S)-7-(3,4-methylenedioxyphenyl)-7'-(4-hydroxy-(3-methoxyphenyl)-8,8'-dimethylbutane]] represented by Chemical Formula 1 below wherein $R_1$ in Formula 1 represents a methoxy group, $R_2$ represents a hydroxyl group, and $R_3$ represents

[Chemical Formula 1]

The inventive lignan compounds may be used in the form of salts, and preferably, pharmaceutically acceptable salts. It is desirable that these salts formed are pharmaceutically acceptable acid addition salts with free acids. As the free acids, organic acids and inorganic acids may be used. Examples of the organic acids include, but are not limited to, citric acid, acetic acid, lactic acid, tartaric acid, maleic acid, fumaric acid, formic acid, propionic acid, oxalic acid, trifluoroacetic acid, benzoic acid, gluconic acid, meta-sulfonic acid, glycolic acid, succinic acid, 4-toluenesulfonic acid, glutamic acid, and aspartic acid. In addition, the examples of the organic acids include, but are not limited to, hydrochloric acid, bromic acid, sulfuric acid, and phosphoric acid.

The inventive lignan compounds can be obtained from plants or their parts by the prior extracting method and isolating method. To obtain the desired extracts, the stems, roots or leaves are either suitably dehydrated and macerated, or simply dehydrated. The desired extracts are then purified by any purification method known to the persons skilled in the art. Moreover, the synthetic compounds or their derivatives corresponding to the lignan compounds represented by Formula 1 are commercially available or can be chemically prepared by a known synthetic method.

The lignan compounds represented by Formula 1 can be isolated and purified from *Myristica fragrance* Houtt. (Jung Yun Lee et al., *Kor. J. Pharmacogn.* 21(4):270-273, 1990). Preferably, the lignan compounds can be isolated and purified from nutmeg or aril. The nutmeg refers to either the ripe fruit of *Myristica fragrance* or a seed present in the fruit. The inventive lignan compounds can be isolated and purified from oil obtained by pressing the nutmeg. Moreover, they may also be isolated and purified from *Myristica argentea* Warb, which is another plant of the Myristicaceae family (Filleur, F. et al., *Natural Product Letters*, 16: 1-7, 2002). In addition, the lignan compounds may also be isolated and purified from *Machilus thunbergii* (Park B. Y. et al., *Biol. Pharm. Bull.*, 27(8): 1305-1307, 2004), and *Leucas aspera* (Sadhu, S. K. et al., *Chem. Pharm. Bull.*, 51(9): 595-598, 2003).

Extraction solvents which can be used for the isolation of the inventive lignan compounds include water and $C_1$-$C_6$ organic solvents. Preferably, these extraction solvents may be used in the forms of purified water, methanol, ethanol, propanol, isopropanol, butanol, acetone, ether, benzene, chloroform, ethyl acetate, methylene chloride, hexane, cyclohexane, petroleum ether or the mixture thereof. These extraction solvents may be used alone or in a mixture of two or more. Isolation and purification of the inventive lignan compounds from the extract of *Myristica fragrance* can be performed by column chromatography packed with various synthetic resins, such as silica gel or active alumina, high performance liquid chromatography (HPLC), etc., or a combination thereof. However, it is understandable that methods for the extraction, isolation, and purification of the inventive lignan compounds do not need to be limited to the above-described methods.

The inventive lignan compounds may be used in the form of either pure compounds after isolation and purification or extracts containing them. For example, the lignan compounds may be used either in the form of extracts from the seeds, fruits, or arils of *Myristica fragrance* or in the form of oil obtained by pressing the seeds of *Myristica fragrance*. As described above, these extracts may be obtained by extracting *Myristica fragrance* with water or $C_1$-$C_6$ organic solvents. Preferably, these extracts may be extracts from the seed of *Myristica fragrance*, i.e., nutmeg extracts.

In one embodiment of the present invention, macelignan represented by Chemical Formula 1, a typical compound of lignan compounds represented by Formula 1, was isolated and purified from ethanol extracts from the seed of *Myristica fragrance* (nutmeg) (see Example 1).

The inventive lignan compounds represented by Formula 1 show excellent antibacterial activity against acne-causing bacteria, including *Propionibacterium acnes* and are so excellent in thermal stability as to maintain their antibacterial activity even upon heating (see Example 3).

Figure 6:
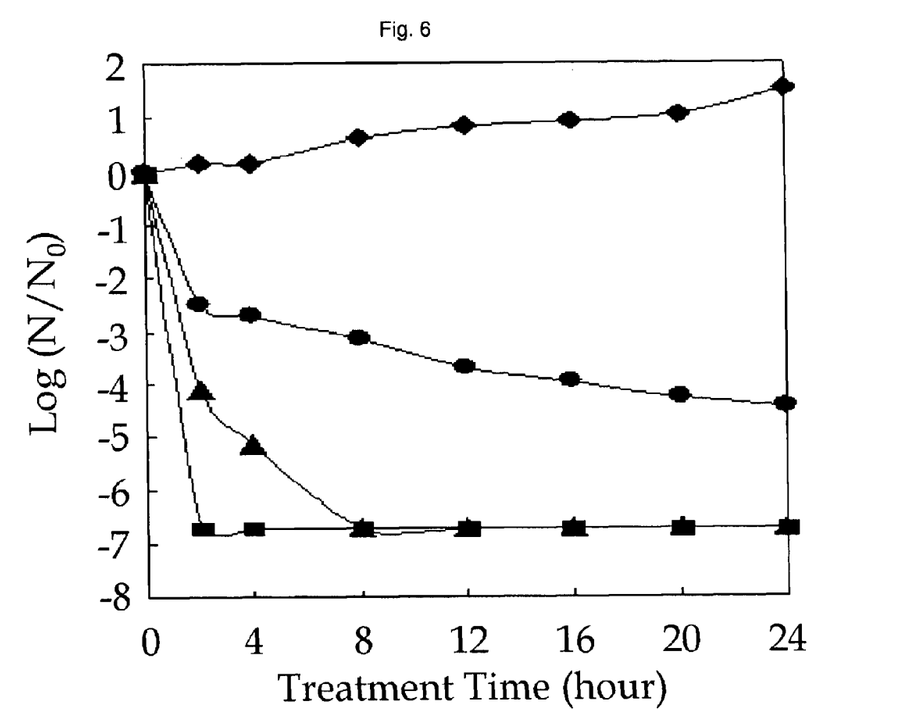
FIG. 6 graphically shows the results of viable cell counting, which indicate the antibacterial activity of the inventive lignan compounds against *Propionibacterium acnes*.
☐: dimethylsulfoxide, a control group;
■: a sample with a macelignan concentration of 0.002%;
▲: a sample with a macelignan concentration of 0.001%; and
●: a sample with a macelignan concentration of 0.0005%.

Antibacterial activity of the inventive lignan compounds against acne-causing bacteria, such as *Propionibacterium acnes*, *Staphylococcus aureus* and *Staphylococcus epidermis*, was tested, and the results indicate high antibacterial activity (see FIG. 6 and Table 2). Particularly, the minimum inhibitory concentration (MIC) of the compounds against *Propionibacterium acnes*, known as the main bacteria causing acne, was determined to be 2 µg/ml, suggesting that the inventive lignan compounds are excellent in antibacterial activity as compared to currently used agents for treating acne. Namely, it is known that the minimum inhibitor concentration (MIC) against *Propionibacterium acnes* of benzoyl peroxide used as an acne treatment agent in the prior art was 500-1000 µg/ml (Decker, L C. et al., *Antimicro. Agents. Chemother.*, 33(3): 326-330, 1989), MIC of benzalkonium chloride was 200~300 µg/ml (Gloor, M. et al., *Arch. Dermatol. Res.*, 265(2): 207-212, 1979), and MIC of terpinen-4-ol, the oil component of tea trees, was 300-500 µg/ml (Raman, A. et al., *Lett. Appl. Microbiol.*, 21(4): 242-245, 1995). In view of these reports, it can be found that the inventive lignan compounds show a much superior antibacterial activity against acne-causing bacteria to the known acne treatment agents. Furthermore, the inventive lignan compounds showed at least 30 times higher antibacterial activity against *Propionibacterium acnes* than crude nutmeg extracts having a minimum inhibitory concentration of 64 µg/ml (see Comparative Example 1). In addition, toilet water and cream, which contain the inventive lignan compounds, were prepared and tested for antibacterial activity, and the test results indicated that the toilet water and the cream were very excellent in antibacterial activity against acne-causing bacteria (see Tables 5 and 7).

These results suggest that the inventive lignan compounds are excellent in antibacterial activity against acne-causing bacteria, *Propionibacterium acnes*, *Staphylococcus aureus*, and *Staphylococcus epidermis*, indicating that they have acne treatment effects. This antibacterial activity of the inventive lignan compounds represented by Formula 1 against the acne-causing bacteria was first identified in the present invention. Furthermore, it can be found that the inventive lignan compounds have a much higher antibacterial activity than that of compounds known as acne treatment agents. Therefore, the inventive lignan compounds can be used as acne treatment agents having a more excellent effect than that of the prior acne treatment agents.

Accordingly, an antibacterial composition and an acne treatment composition, which contain, as the active ingredients, the lignan compounds represented by Formula 1 or their pharmaceutically acceptable salts, may be administered orally or parenterally in clinical trials and used in the form of conventional drug preparations.

When the inventive compounds are formulated in the form of conventional preparations, they are formulated with commonly used diluents or excipients, such as fillers, vehicles, binders, wetting agents, disintegrants, and surfactants. Solid formulations for oral administration include tablets, pills, powders, granules, and capsules, and these solid formulations are prepared by mixing the lignan compounds with at least one excipient, for example, starch, calcium carbonate, sucrose, lactose, or gelatin. In addition to simple excipients, lubricants such as magnesium stearate or talc may also be used. Liquid formulations for oral administration include suspensions, internal solutions, emulsions and syrups, which contain various excipients, such as wetting agents, sweeting agents, aromatics, and preservatives, as well as commonly used simple diluents, such as water, liquid paraffin, and the like. Formulations for parenteral administration include sterilized aqueous solution, non-aqueous solvents, suspensions, emulsions, freeze-dried formulations, ointments, and creams. As non-aqueous solvents and suspensions, vegetable oils, such as propylene glycol, polyethylene glycol and olive oil, and injectable esters, such as ethyl oleate and the like, may be used.

In addition, the inventive antibacterial composition and acne treatment composition may be administered parenterally by subcutaneous, intravenous, intramuscular, or intrathoracic injection. In order to formulate the inventive compounds into preparations for parenteral administration, the lignan compounds of Formula 1 are mixed with a stabilizer or buffer in water to prepare a solution or suspension which is then formulated into unit dose vials or ampoules. A dose unit contains, for example, 1, 2, 3 or 4 times, or ½, ⅓ or ¼ times a single dose. The single dose preferably contains a one-time dose of active ingredients, which corresponds to all, ½, ⅓ or ¼ times a daily dose.

The effective dose of the lignan compounds represented by Formula 1 is 0.1-50 mg/kg/time, preferably 1-10 mg/kg/time, and can be administered 1-3 times a day. The dose level for certain patients may vary depending on the body weight, age, sex, health condition, diet, excretion and disease severity of patients, and administration time and route.

The inventive lignan compounds represented by Formula 1 were tested for toxicity in oral administration to mice, and the test results indicated that the 50% lethal dose ($LD_{50}$) of the compounds was more than 2,000 mg/kg.

Particularly, the inventive antibacterial composition or acne treatment composition containing the lignan compounds represented by Formula 1 can be formulated into preparations for skin application, such as ointments or cream. The inventive lignan compounds can be used added suitably depending on the formulation of a preparation for acne skin within a range of 0.001-10.0% by weight, and preferably 0.001-5.0% by weight, based on the total weight of the preparation. The addition of the lignan compounds at the amount of less than 0.001% by weight leads to a reduction in antibacterial activity, and the addition of the compounds at an amount of more than 10.0% by weight does not show a great increase in antibacterial activity while increasing only their addition amount.

Antibacterial agents against acne-causing bacteria, and acne treatment agents, which contain the inventive lignan compounds represented by Formula 1, include cosmetics for acne skin. The cosmetics for acne skin include cleaners, such as soaps, creams and toilet waters.

The cosmetics containing the inventive lignan compounds represented by Formula 1 may be prepared in various forms, including cleaners, such as soaps, liquid and cream type facial cleaners, creams, toilet waters, gels, aqueous-soluble liquid, essence, oil-in-water emulsions or water-in-oil emulsions. And the suitable preparations containing the inventive lignan compounds can be easily determined by any person skilled in the art. Also, the inventive lignan compounds may be used as cosmetics for acne skin by adding them to foundation cosmetics, such as foam cleansing, lotion, essence, etc.

The inventive lignan compounds represented by Formula 1 can be added suitably depending on the formulation of a cleanser or cosmetic within a range of 0.001-10.0% by weight, and preferably 0.001-5.0% by weight, based on the total weight of the cleanser or cosmetic. The addition of the lignan compounds at the amount of less than 0.001% by weight leads to a reduction in antibacterial activity, and the addition of the compounds at the amount of more than 10.0% by weight does not show a great increase in antibacterial activity while increasing only their addition amount.

BEST MODE FOR CARRYING OUT THE INVENTION

Hereinafter, the present invention will be described in detail by the following examples.

It is understandable, however, that these examples are given for illustrative purpose only and are not construed to limit the scope of the present invention. In the following examples and test examples, all percentages are by weight unless otherwise stated. In addition, all analyses of activity were repeated more than three times, and the results were expressed as mean±standard deviation. The statistical analysis was performed by the Student's t-test, and p values<0.05 were considered to be statistically significant.

Example 1

Isolation and Purification of Lignan Compounds from Nutmeg

<1-1> Isolation and Purification of Macelignan 400 ml of 75 volume % ethanol was added to 100 g (dry weight) of dried and crushed nutmeg, and the solution was left to stand at ambient temperature for 2 days and filtered through Whatman filter paper No. 2. These procedures were repeated two times, and then the ethanol filtrate was concentrated under vacuum, freeze-dried, and eluted by silica gel column chromatography using a solvent mixture of hexane and ethyl acetate (20:1). The solvent was completely removed by a vacuum rotary concentrator so as to obtain a crude nutmeg extract. The crude nutmeg extract was separated on a TLC plate with a solvent system of hexane and ethyl acetate (10:1) and confirmed by TLC plate analysis. After the ratio of the development distance of the confirmed antibacterial active substance to the development distance of the hexane-ethyl acetate solvent system was adjusted to 0.2, thin layer chromatography (TLC; RP-18 gel 60F$_{254}$, Merck) was performed using a developing solvent of methanol and water (8:2) (v/v), thus isolating a single substance having Rf=0.2 and strong absorption bands at UV wavelengths (254, 365 nm, VL-6-LC, Vilber lourmat).

<1-2> Analysis of Structure

Figure 1:
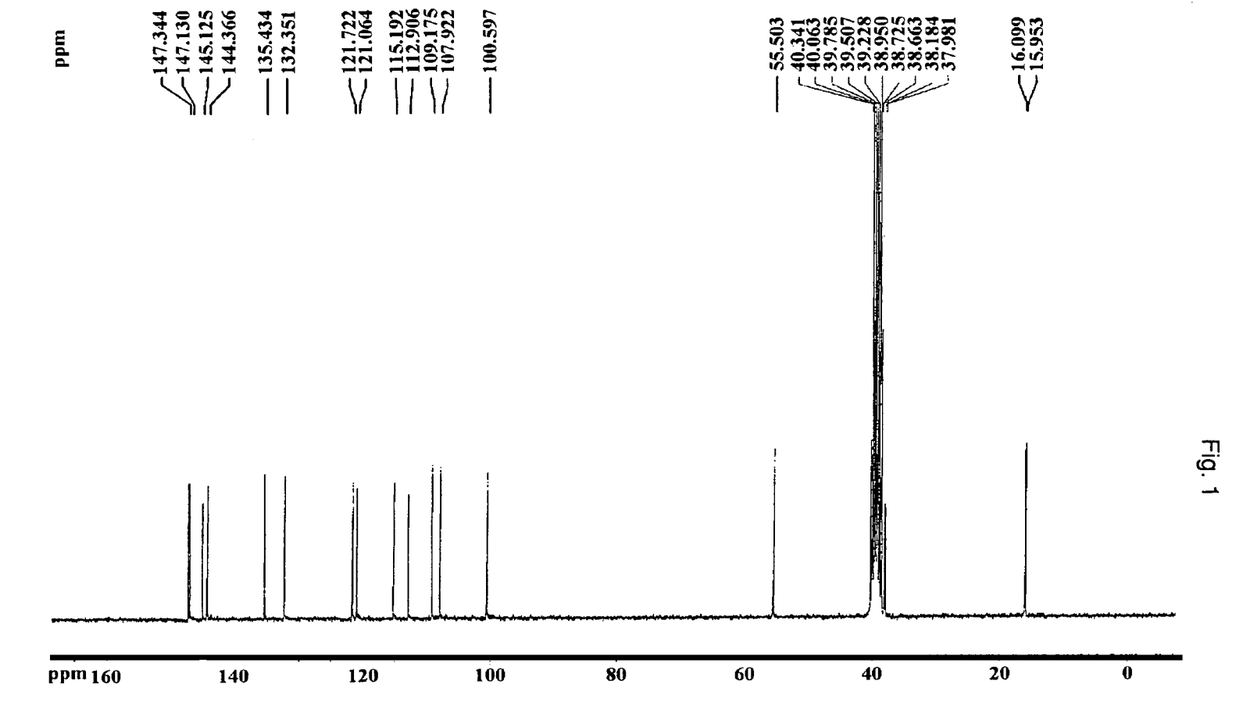
FIG. 1 shows the $^{13}$C-NMR spectrum of the inventive lignan compounds.
Figure 2:
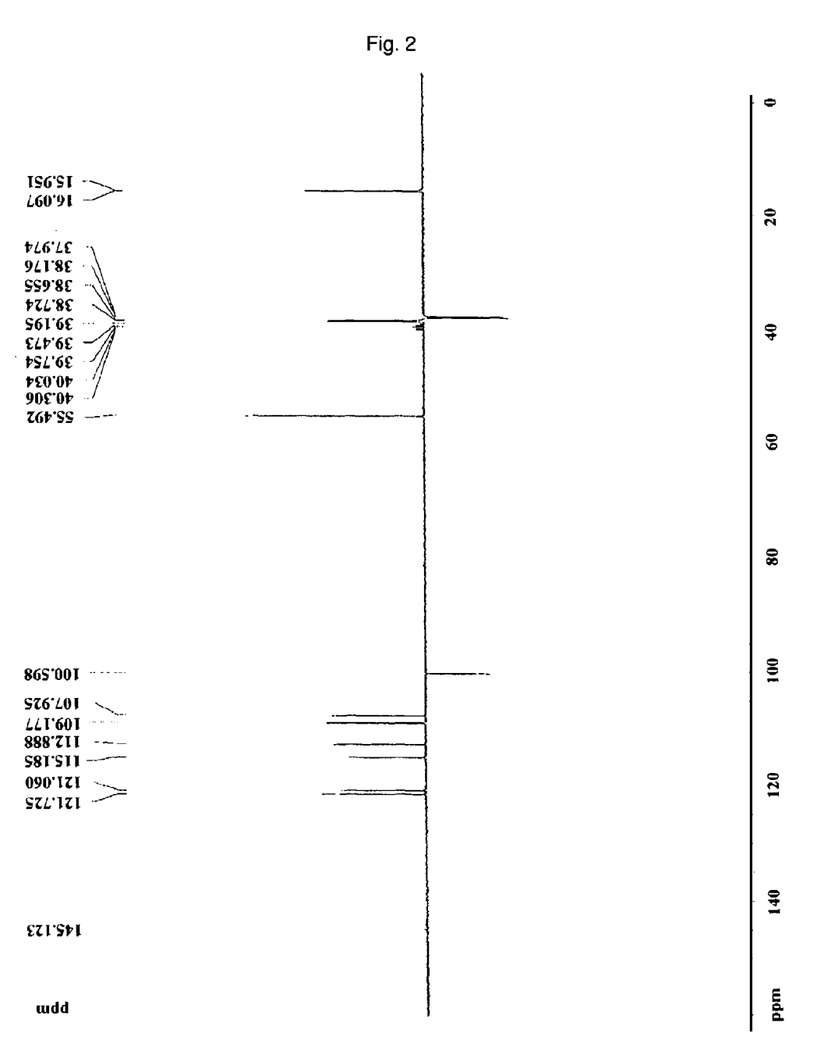
FIG. 2 shows the $^1$H-NMR spectrum of the inventive lignan compounds.
Figure 3:
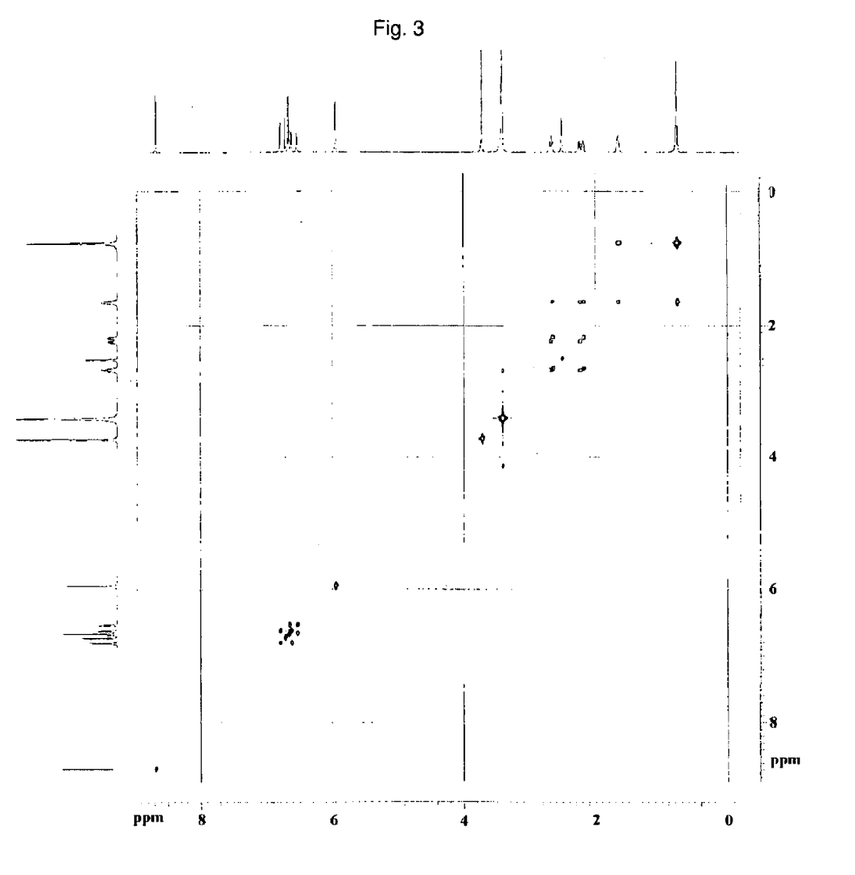
FIG. 3 shows the $^1$H-$^1$H COSY spectrum of the inventive lignan compounds.
Figure 4:
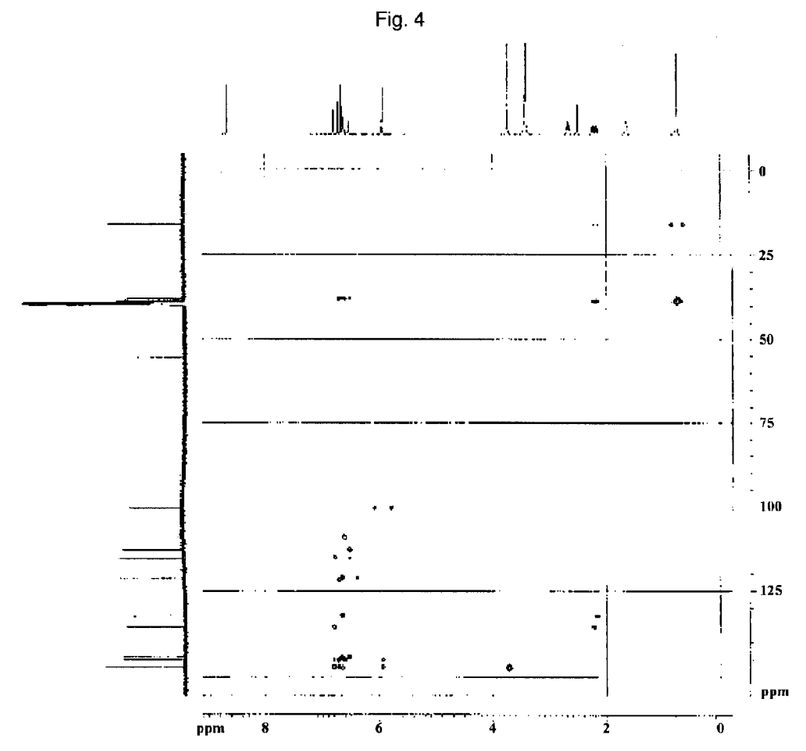
FIG. 4 shows the $^1$H-$^{13}$C HMBC spectrum of the inventive lignan compounds.

In order to determine the structure of the single substance isolated in Example 1-1, the $^1$H-NMR and $^{13}$C-NMR spectra of the isolated single substance were measured at 600 MHz and 150 MHz, respectively, in DMSO. The measurement results are shown in FIGS. 1 and 2, respectively. In order to measure $^1$H-$^1$H correlation and $^1$H-$^{13}$C correlation on the basis of the results of $^{13}$C-NMR and $^1$H-NMR spectra, the $^1$H-$^1$H COSY and $^1$H-$^{13}$C HMBC spectra of the single substance were measured and the results are shown in FIGS. 3 and 4. respectively. The results of the $^1$H-NMR, $^{13}$C-NMR, $^1$H-$^1$H COSY and $^1$H-$^{13}$C HMBC spectra are summarized in Table 1 below.

TABLE 1

| Position | $^{13}$C-NMR | $^1$H-NMR | $^1$H-$^1$H COSY | $^1$H-$^{13}$C HMBC |
|---|---|---|---|---|
| 1 | 135.4 | | | |
| 2 | 109.2 | 6.72 brs | | C-7, C-6, C-4, C-3 |
| 3 | 147.3 | | | |
| 4 | 145.1 | | | |
| 5 | 107.9 | 6.79 d (7.8) | 6.61 | C-6, C-4, C-3, C-1 |

TABLE 1-continued

| Position | $^{13}$C-NMR | $^{1}$H-NMR | $^{1}$H-$^{1}$H COSY | $^{1}$H-$^{13}$C HMBC |
|---|---|---|---|---|
| 6 | 121.7 | 6.61 dd (7.8) | 6.79 | C-7, C-5, C-4, C-2, C-1 |
| 7 | 38.2 | 2.23 dd (13.2, 9.3) | 1.64, 2.66 | C-8, C-6, C-2, C-1 |
|   |       | 2.66 dd (13.2, 4.8) | 1.64, 2.23 | C-9, C-8, C-6, C-2, C-1 |
| 8 | 38.7 | 1.64 brs | 0.75, 2.23, 2.66 | C-7 |
| 9 | 16.0 | 0.75 d (6.3) | 1.64 | C-8, C-7 |
| 1' | 132.4 | | | |
| 2' | 112.9 | 6.66 brs | | C-7', C-6', C-4', C-3' |
| 3' | 147.1 | | | |
| 4' | 144.4 | | | |
| 5' | 115.2 | 6.66 d (7.9) | 6.53 | C-6', C-4', C-3', C-1' |
| 6' | 121.0 | 6.53 d (7.9, 1.1) | 6.66 | C-7', C-5', C-4', C-2', C-1' |
| 7' | 38.0 | 2.17 dd (13.2, 9.3) | 1.64, 2.66 | C-8', C-6', C-2', C-1' |
|    |      | 2.66 dd (13.2, 4.8) | 1.64, 2.17 | C-9', C-8', C-6', C-2', C-1' |
| 8' | 38.7 | 1.64 brs | 0.75, 2.17, 2.66 | C-7' |
| 9' | 16.1 | 0.75 d (6.3) | 1.64 | C-8', C-7' |
| OMe | 55.5 | 3.72 (s) | | |
| O—CH$_2$—O | 100.6 | 5.95 d (4.8) | | C-3, C-4 |

<1-3> Mass Spectrometry

Figure 5:
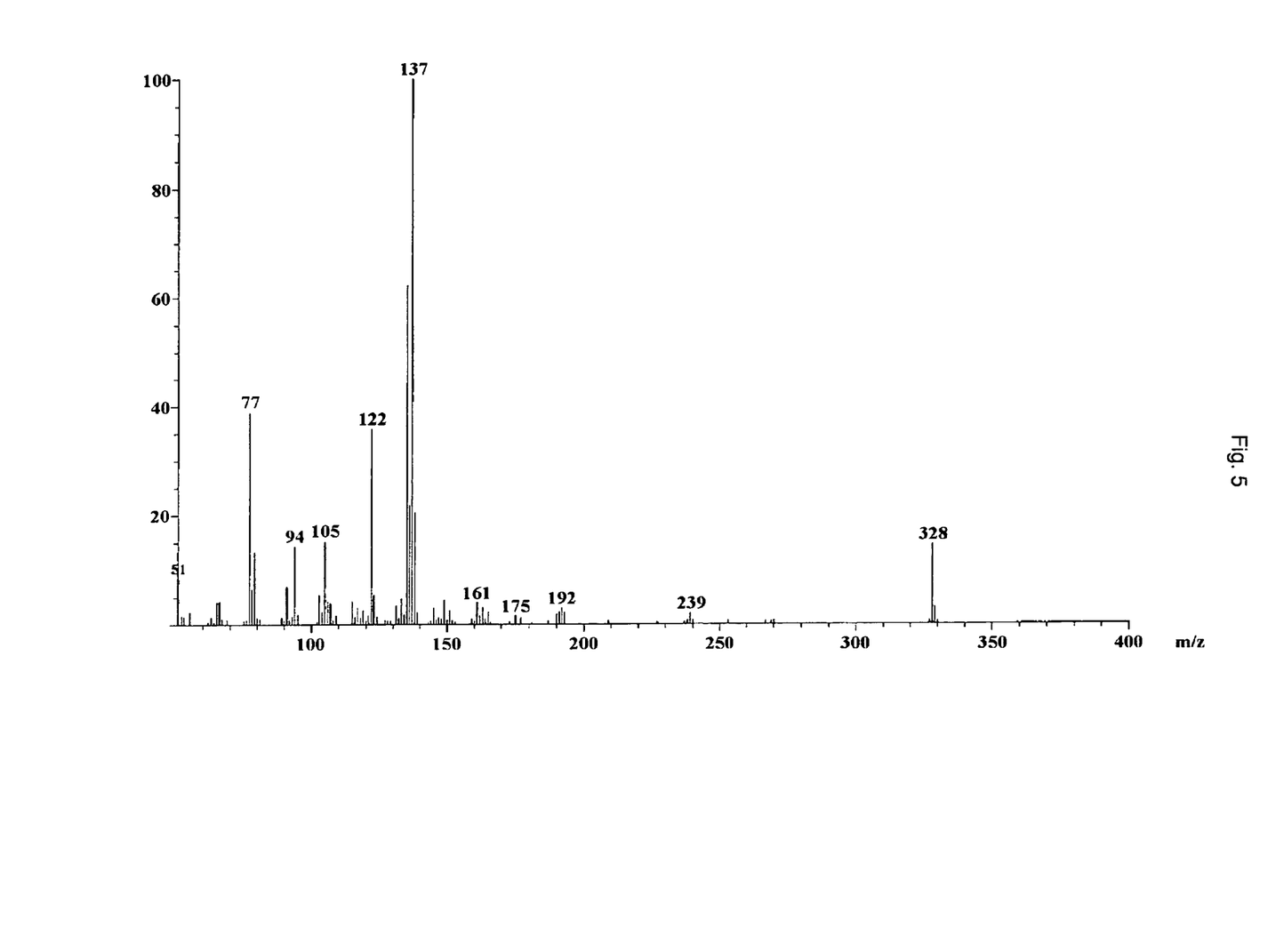
FIG. 5 shows the EI-Mass spectrum of the inventive lignan compounds.

The result of EI/MS spectrum of the isolated single substance is also shown in FIG. 5. In EI/MS, the [M]$^+$ of this single substance was observed at m/z 328, indicating that it has a molecular weight of 328. The molecular formula of the single substance was $C_{20}H_{24}O_4$.

By analyzing the $^1$H-NMR, $^{13}$C-NMR, $^1$H-$^1$H COSY, $^1$H-$^{13}$C HMBC and EI/MS spectra, and comparing with previously published reports (Woo, W. S. et al., *Phytochemistry*, 26: 1542-1543, 1987), the single substance isolated in Example 1-1 was determined to be a macelignan compound.

Example 2

Antibacterial Activity Test

<2-1> Measurement of Effect of Lignan Compound on Growth Inhibition of Acne-Inducing Bacteria, by Viable Cell Counting The macelignan compound prepared in Example <1-1> was dissolved in dimethylsulfoxide to concentrations of 0.002%, 0.001% and 0.0005%, respectively. 100 µl of *Propionibacterium acnes* diluted to 2×10$^5$ CFU/ml was added to test tubes containing the macelignan solutions and allowed to react at 37° C. for 2 hr, 4 hr, 8 hr, 12 hr, 16 hr, 20 hr, and 24 hr. Each sample was serially diluted 10-fold and subjected to the pour plate method. The plates were cultured in an incubator at 37° C. and measured for viable cell colonies of *Propionibacterium acnes*. The results are graphically shown in FIG. 6.

As shown in FIG. 6, the results of the viable cell counting demonstrated that the bacteria were almost dead within 2 hours at a macelignan compound concentration of 0.002% (20 µg/ml) and within 8 hours at a macelignan compound concentration of 0.001% (10 µg/ml). These results suggest that, in view of the fact that oral drugs are administered commonly at 8-hr intervals, and ointments or application drugs are used at about 2-4-hr intervals, the use of macelignan compound-containing oral drugs or skin-application drug as acne treatment agents can provide antibacterial activity against *Propionibacterium acnes*, that is typical acne-causing bacteria.

<2-2> Measurement of Minimum Inhibitory Concentration (MIC) of Lignan Compounds

The macelignan compound prepared in Example <1-1> was dissolved in 0.5% methanol, and 1 ml of BHI (Brain Heart Infusion) broth was placed into each of test tubes. 1 ml of 2% macelignan solution was placed only into the first test tube and serially diluted 2-fold. Then, 100 µl of *Propionibacterium acnes* were added at 2×10$^5$ CFU/ml to each test tube and cultured at 37° C. for at least 24 hours. The minimum inhibitory concentration of the macelignan compound against *Propionibacterium acnes* was determined as the lowest concentration which did not show opacity, and the result is shown in Table 2 below. Using the same method, the minimum inhibitory concentrations against *Staphylococcus aureus* and *Staphylococcus epidermis* were also measured and the results are shown in Table 2.

TABLE 2

| | Minimum inhibitory concentrations against acne-causing bacteria (unit: µg/ml) | | |
|---|---|---|---|
| | *Propionibacterium acnes* | *Staphylococcus aureus* | *Staphylococcus epidermis* |
| Macelignan | 2 | 125 | 64 |

Comparative Example 1

Antibacterial Activity Test of Crude Nutmeg Extract

Figure 7:
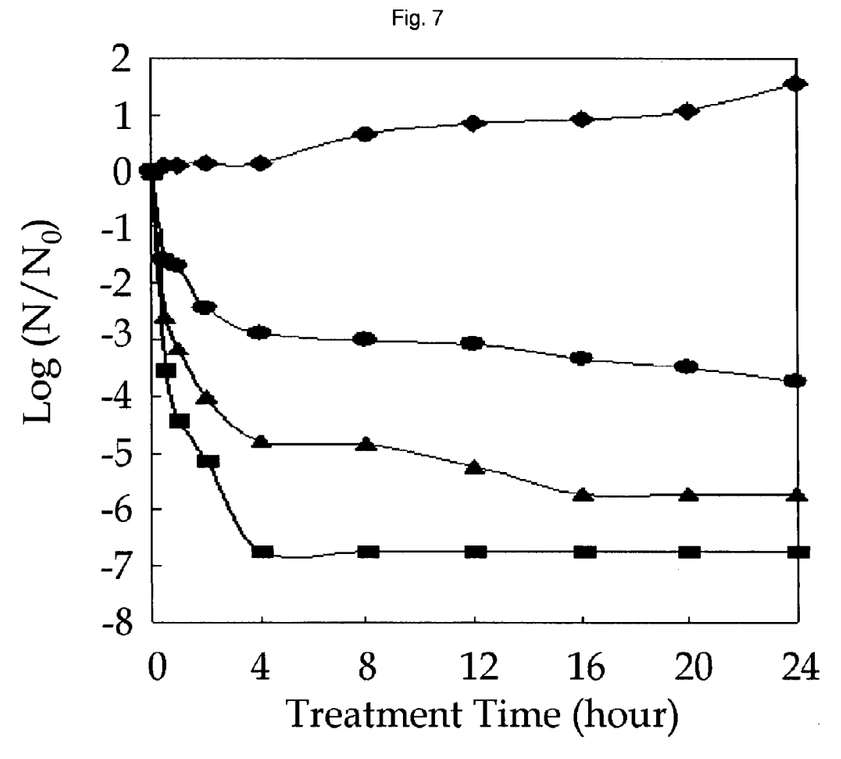
FIG. 7 graphically shows the results of viable cell counting, which indicate the antibacterial activity of the inventive crude extracts of nutmeg against *Propionibacterium acnes*.
☐: dimethylsulfoxide, a control group;
■: a sample with a crude nutmeg extract concentration of 0.02%;
▲: a sample with a crude nutmeg extract concentration of 0.01%; and
●: a sample with a crude nutmeg extract concentration of 0.005%.

Inhibitory effects on growth of the acne-causing bacteria were measured using the crude nutmeg extract prepared during the isolation procedure of macelignan in Example <1-1>, in the same manner as in Example <2-1>, and the results are shown in FIG. 7. Moreover, the minimum inhibitory concentrations of the crude nutmeg extract against the acne-causing bacteria were measured, and as a result, the minimum inhibitory concentrations against *Propionibacterium acnes*, *Staphylococcus aureus*, and *Staphylococcus epidermis* were 64 µg/ml, 250 µg/ml, and 250 µg/ml, respectively.

Example 3

Thermal Stability of Lignan Compounds

The macelignan compound prepared in Example <1-1> was dissolved in dimethylsulfoxide to a concentration of 0.1%. The sample was thermally treated for 30 minutes at different temperatures of 60° C., 70° C., 80° C., 90° C., 100° C., and 121° C. and measured for antibacterial activity by the well diffusion assay. The results are shown in Table 3 below.

TABLE 3

| Treatment temperature (° C.) | 60 | 70 | 80 | 90 | 100 | 121 |
|---|---|---|---|---|---|---|
| Diameter (mm) of clear zone on the plate containing macelignan | 17 | 16 | 17 | 17 | 18 | 17 |

As can be seen in Table 3, the macelignan compound showed little or no reduction in antibacterial activity even after thermal treatment at a temperature range of 60° C.-121° C. This suggests that the inventive lignan compounds are stable even in high-temperature treatment procedures.

Example 4

Preparation of Macelignan-Containing Toilet Water and Antibacterial Activity Test Thereof <4-1> Preparation of Macelignan-Containing Toilet Water Using the inventive macelignan compound, toilet waters having compositions shown in. Table 4 below were prepared. The macelignan compound isolated in Example <1-1> was dissolved in water at four concentrations of 1.0%, 0.1%, 0.01%, and 0.001%, followed by mixing with aqueous solution of phosphoric acid. Ethanol, glycerin, and propylene glycol were mixed and added to the above-prepared mixture, to which perfume and preservatives were added. The resulting mixture was adjusted for weight with purified water and homogenized.

TABLE 4

| Samples | 1 | 2 | 3 | 4 |
|---|---|---|---|---|
| Main components | 1.0% of macelignan<br>2.0% of glycerin<br>2.0% of propylene glycol<br>0.1% of potassium phosphate<br>0.05% of disodium phosphate<br>0.02% of perfume<br>50% of ethanol (96%)<br>The balance of purified water<br>0.1% of preservative | 0.1% of macelignan<br>2.0% of glycerin<br>2.0% of propylene glycol<br>0.1% of potassium phosphate<br>0.05% of disodium phosphate<br>0.02% of perfume<br>50% of ethanol (96%)<br>The balance of purified water<br>0.1% of preservative | 0.01% of macelignan<br>2.0% of glycerin<br>2.0% of propylene glycol<br>0.1% of potassium phosphate<br>0.05% of disodium phosphate<br>0.02% of perfume<br>50% of ethanol (96%)<br>The balance of purified water<br>0.1% of preservative | 0.001% of macelignan<br>2.0% of glycerin<br>2.0% of propylene glycol<br>0.1% of potassium phosphate<br>0.05% of disodium phosphate<br>0.02% of perfume<br>50% of ethanol (96%)<br>The balance of purified water<br>0.1% of preservative |

<4-2> Antibacterial Activity Test 1 ml of solution containing the acne-causing bacteria, such as *Propionibacterium acnes*, was added to test tubes containing 4 ml of each of the macelignan-containing toilet water prepared in Example <4-1>. The solution was cultured with shaking, and antibacterial activity was measured by viable cell counting after 24 hours. The results are shown in Table 5 below.

TABLE 5

| Acne-causing bacteria | Samples | Viable cell number (cells/ml) 0 hr | 24 hr |
|---|---|---|---|
| *Propionibacterium acnes* | 1 | $3.0 \times 10^5$ | <1 |
| | 2 | $3.0 \times 10^5$ | <1 |
| | 3 | $3.0 \times 10^5$ | <1 |
| | 4 | $3.0 \times 10^5$ | $1.2 \times 10^2$ |
| | Toilet water containing no macelignan | $3.0 \times 10^5$ | $3.1 \times 10^3$ |
| *Staphylococcus aureus* | 1 | $4.5 \times 10^5$ | <1 |
| | 2 | $4.5 \times 10^5$ | <1 |
| | 3 | $4.5 \times 10^5$ | <1 |
| | 4 | $4.5 \times 10^5$ | $3.1 \times 10^2$ |
| | Toilet water containing no macelignan | $4.5 \times 10^5$ | $4.7 \times 10^3$ |
| *Staphylococcus epidermis* | 1 | $6.8 \times 10^5$ | <1 |
| | 2 | $6.8 \times 10^5$ | <1 |
| | 3 | $6.8 \times 10^5$ | <1 |
| | 4 | $6.8 \times 10^5$ | $3.5 \times 10^2$ |
| | Toilet water containing no macelignan | $6.8 \times 10^5$ | $5.1 \times 10^3$ |

As can be seen in Table 5, the toilet waters containing macelignan were very high in antibacterial activity against the acne-causing bacteria, including *Propionibacterium acnes*, as compared to that of the samples containing no macelignan.

Example 5

Preparation of Macelignan-Containing Creams and Antibacterial Activity Test thereof <5-1> Preparation of Macelignan-Containing Creams Creams having compositions shown in Table 6 below were prepared using the inventive macelignan compound. First, substances indicated as "B" in Table 6 were melted at 75-80° C., and substances indicated as "C" were melted at the same temperature. Macelignan compound indicated as "A" was added at different concentrations of 3.0%, 0.1%, 0.01% and 0.001% to the solution of "C" emulsified in the solution of "B". Then, the mixture was added with perfume and adjusted to the desired weight with purified water.

TABLE 6

| Samples | | 5 | 6 | 7 | 8 |
|---|---|---|---|---|---|
| Main component | A | 3.0% of macelignan | 0.1% of macelignan | 0.01% of macelignan | 0.001% of macelignan |
| | B | 2.0% of glycerin 2.0% of propylene glycol 8.0% of lauryl chloride sulfide 5.4% of stearin 4.5% of mineral oil | 2.0% of glycerin 2.0% of propylene glycol 8.0% of lauryl chloride sulfide 5.4% of stearin 4.5% of mineral oil | 2.0% of glycerin 2.0% of propylene glycol 8.0% of lauryl chloride sulfide 5.4% of stearin 4.5% of mineral oil | 2.0% of glycerin 2.0% of propylene glycol 8.0% of lauryl chloride sulfide 5.4% of stearin 4.5% of mineral oil |
| | C | 0.02% of perfume 6.5% of cetyl alcohol The balance of purified water 0.1% of preservatives | 0.02% of perfume 6.5% of cetyl alcohol The balance of purified water 0.1% of preservatives | 0.02% of perfume 6.5% of cetyl alcohol The balance of purified water 0.1% of preservatives | 0.02% of perfume 6.5% of cetyl alcohol The balance of purified water 0.1% of preservatives |

Example 5-2> Antibacterial Activity Test 1 ml of solution containing the acne-causing bacteria, such as Propionibacterium acnes, was added to test tubes containing 4 ml of each of the macelignan-containing creams prepared in Example <5-1>. The solution was cultured with shaking, and measured for antibacterial activity by viable cell counting after 24 hours. The results are shown in Table 7 below.

TABLE 7

| | | Viable cell number (cells/ml) | |
|---|---|---|---|
| Acne-causing bacteria | Samples | 0 hr | 24 hr |
| Propionibacterium acnes | 5 | $3.0 \times 10^5$ | <1 |
| | 6 | $3.0 \times 10^5$ | <1 |
| | 7 | $3.0 \times 10^5$ | <1 |
| | 8 | $3.0 \times 10^5$ | $11.5 \times 10^2$ |
| | Cream containing no macelignan | $3.0 \times 10^5$ | $3.3 \times 10^3$ |
| Staphylococcus aureus | 5 | $4.5 \times 10^5$ | <1 |
| | 6 | $4.5 \times 10^5$ | <1 |
| | 7 | $4.5 \times 10^5$ | <1 |
| | 8 | $4.5 \times 10^5$ | $3.4 \times 10^2$ |
| | Cream containing no macelignan | $4.5 \times 10^5$ | $4.1 \times 10^3$ |
| Staphylococcus epidermis | 5 | $6.8 \times 10^5$ | <1 |
| | 6 | $6.8 \times 10^5$ | <1 |
| | 7 | $6.8 \times 10^5$ | <1 |
| | 8 | $6.8 \times 10^5$ | $4.3 \times 10^2$ |
| | Cream containing no macelignan | $6.8 \times 10^5$ | $5.1 \times 10^3$ |

As can be seen in Table 7, the inventive creams were very high in antibacterial activity against the acne-causing bacteria, including Propionibacterium acnes, as compared to that of the samples containing no macelignan.

Example 6

Clinical Tests of Lignan Compounds on Acne Patients
<6-1> Oral Administration

The macelignan isolated and purified in Example <1-1> was clinically tested for acne treatment.
30 men and women in their mid-30s, who suffer from acne, were selected as test subjects. The macelignan was administered to the test subjects at 600 mg two times a day for 4 weeks. The results are shown in Table 8 below. The number of lesions after 4 weeks of administration was remarkably reduced as compared to the number of lesions before administration, and this reduction was statistically significant (p-value<0.05).

TABLE 8

Measurement of acne lesion number in oral administration

| | Mean number before administration | Mean number after 4 weeks of administration | p-value |
|---|---|---|---|
| Comedos | 18.92 | 7.94 | 0.0073 |
| Papules | 14.47 | 5.69 | 0.013 |
| Pustules | 5.92 | 2.30 | 0.037 |
| Nodules | 0.74 | 0.24 | 0.0215 |

6-2: Application to Skin

The macelignan-containing cream prepared in Example <5-1> was clinically tested for the prevention and treatment of acne. 30 men and women test subjects in their mid-teens to mid-thirties, who suffer from acne, were selected as test subjects. The cream was applied to the skin of the test subjects in a defined amount two times a day for 4 weeks. The results are shown in Table 9 below. The number of lesions after 4 weeks of skin application was remarkably reduced as compared to the number of lesions before skin application, and this reduction was statistically significant (p-value<0.05).

TABLE 9

Measurement of acne lesion number in application to skin

| | Mean number before administration | Mean number after 4 weeks of administration | p-value |
|---|---|---|---|
| Comedos | 19.74 | 5.21 | 0.0083 |
| Papules | 18.40 | 6.17 | 0.0024 |
| Pustules | 6.24 | 2.37 | 0.0231 |
| Nodules | 0.73 | 0.26 | 0.034 |

<Preparation 1>
Preparation of Inventive Acne Treatment Agent
<1-1> Preparation of Tablets 25 mg of the inventive macelignan, 26 mg of lactose, an excipient for direct tableting, 3.5 mg of Avicel (microcrystalline cellulose), 1.5 mg of sodium starch glycolate, a disintegrant, and 8 mg low-hydroxypropylcellulose (L-HPC) for direct tableting, a binder, were mixed with each other in a U-shaped mixer for 20 minutes. After completion of mixing, the mixture was added with 1 mg of magnesium stearate, a lubricant, and further mixed for 3 minutes. Through a quantitative test and a constant humidity test, the mixture was then tableted and film-coated to obtain tablets.

<1-2> Preparation of Syrup

A syrup containing 2% (w/v) of the inventive macelignan or its pharmaceutically acceptable salt as an active ingredient was prepared in the following manner: 2 g of an acid addition salt of the inventive macelignan, 0.8 g of saccharin, and 25.4 g of sugar were dissolved in 80 g of hot water. The solution was cooled, to which 8.0 g of glycerin, 0.04 g of flavoring, 4.0 g of ethanol, 0.4 g of sorbic acid, and a suitable amount of distilled water were then added. The mixture was added with water to a total volume of 100 ml.

<1-3> Preparation of Capsules 50 mg of the inventive macelignan, 50 mg of lactose, 46.5 mg of starch, 1 mg of talc, and a suitable amount of magnesium stearate were mixed with each other. The mixture was packed into hard gelatin capsules to obtain capsules.

<1-4> Preparation of Injection Solution

An injection solution containing 10 mg of the macelignan was prepared in the following manner: 1 g of a hydrochloride salt of the inventive macelignan, 0.6 g of sodium chloride, and 0.1 g of ascorbic acid were dissolved in distilled water to prepare 100 ml of a solution. The solution was poured in a bottle and sterilized by heating for 30 minutes at 20° C.

INDUSTRIAL APPLICABILITY

As described above, the lignan compounds represented by Formula 1 are excellent not only in antibacterial activity against acne-causing bacteria, including *Propionibacterium acnes, Staphylococcus epidermis* and *Staphylococcus aureus*, but also in thermal stability. Accordingly, the inventive lignan compounds may be very useful as antibacterial agents against the acne-causing bacteria, and acne treatment agents.

The invention claimed is:

1. A method for inhibiting the growth of acne-causing bacteria selected from the group consisting of *Propionibacterium acnes, Staphylococcus epidermis* and *Staphylococcus aureus*, the method comprising administering an effective amount of macelignan represented by Chemical Formula 1 to a subject in need thereof:

[Chemical formula 1]

2. A method for treating acne through inhibiting the growth of acne-causing bacteria, comprising administering an effective amount of macelignan represented by Chemical Formula 1 to a subject in need thereof, wherein the acne-causing bacteria are selected from the group consisting of *Propionibacterium acnes, Staphylococcus epidermis* and *Staphylococcus aureus*:

[Chemical formula 1]

* * * * *